US011391719B2

(12) United States Patent
Henck

(10) Patent No.: US 11,391,719 B2
(45) Date of Patent: Jul. 19, 2022

(54) METHODS FOR MEASURING ANALYTES USING NANOFABRICATED DEVICE

(71) Applicant: Roche Sequencing Solutions, Inc., Pleasanton, CA (US)

(72) Inventor: Steven Henck, Mountain View, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 184 days.

(21) Appl. No.: 15/851,608

(22) Filed: Dec. 21, 2017

(65) Prior Publication Data
US 2018/0120287 A1 May 3, 2018

Related U.S. Application Data

(63) Continuation of application No. PCT/EP2016/065155, filed on Jun. 29, 2016.
(Continued)

(51) Int. Cl.
G01N 33/487 (2006.01)
C12Q 1/6869 (2018.01)
G01N 27/447 (2006.01)

(52) U.S. Cl.
CPC ..... G01N 33/48721 (2013.01); C12Q 1/6869 (2013.01); G01N 27/44791 (2013.01)

(58) Field of Classification Search
CPC ....... G01N 33/48721; G01N 27/44791; G01N 27/3275; G01N 27/3278; C12Q 1/6869;
(Continued)

(56) References Cited

U.S. PATENT DOCUMENTS

2004/0248282 A1* 12/2004 Sobha M ............... B82Y 10/00
435/287.2
2013/0281325 A1* 10/2013 Elibol ................ G01N 27/3278
204/406
(Continued)

FOREIGN PATENT DOCUMENTS

WO 2008124706 A2 10/2008
WO 2014059144 A1 4/2014

OTHER PUBLICATIONS

International Search Report dated Oct. 4, 2016 in Application No. PCT/EP2016/065155, pp. 1-12.
(Continued)

Primary Examiner — Maris R Kessel
Assistant Examiner — Vivian A Tran
(74) Attorney, Agent, or Firm — Kilpatrick Townsend & Stockton LLP

(57) ABSTRACT

Devices for sequencing linear biomolecules (e.g., DNA, RNA, polypeptides, proteins, and the like) using quantum tunneling effects, and methods of making and using such devices, are provided. A nanofabricated device can include a small gap formed by depositing a thin film between two electrodes, and subsequently removing the film using an etching process. The width of the resulting gap can correspond with the size of a linear biomolecule such that when a part of the biomolecule (e.g., a nucleobase or amino acid) is present in the gap, a change in tunneling current, voltage, or impedance can be measured and the part of the biomolecule identified. The gap dimensions can be precisely controlled at the atomic-scale by, for example, atomic layer deposition (ALD) of the sacrificial film. The device can be made using existing integrated circuit fabrication equipment and facilities, and multiple devices can be formed on a single chip.

18 Claims, 8 Drawing Sheets

Related U.S. Application Data

(60) Provisional application No. 62/187,161, filed on Jun. 30, 2015.

(58) Field of Classification Search
CPC ...... C12Q 1/68; C12Q 1/6806; C12Q 1/6874; C12Q 2563/116; C12Q 2565/631
See application file for complete search history.

(56) References Cited

U.S. PATENT DOCUMENTS

| | | | | |
|---|---|---|---|---|
| 2014/0190824 | A1* | 7/2014 | Credo | G01N 27/26 204/403.15 |
| 2016/0187282 | A1* | 6/2016 | Gardner | H05K 3/303 204/403.01 |
| 2016/0320364 | A1* | 11/2016 | Ikeda | C23C 16/45525 |
| 2017/0146510 | A1* | 5/2017 | Ikeda | G01N 33/48721 |

OTHER PUBLICATIONS

Ivanov et al, DNA Tunneling Detector Embedded in a Nanopore, NANO Letters, 2011, pp. 279-285, vol. 11 No. 1.

Ivanov et al, On-Demand Delivery of Single DNA Molecules Using Nanopipets, ACS Nano, 2015, pp. 3587-3595, vol. 9, No. 4.

Tian et al, The fabrication and characterization of adjustable nanogaps between gold electrodes on chip for electrical measurement of single molecules, Nanotechnology, Jun. 22, 2010, 274012 (6 pp.), vol. 21, No. 27.

Wang et al., The evolution of nanopore sequencing, Frontiers in Genetics, Jan. 7, 2015, (20 pp.), vol. 5, Art. 449.

Williams et al, Etch Rates for Micromachining Processing—Part II, Journal of Microelectromechanical Systems, Dec. 1, 2003, pp. 761-778, vol. 12, No. 6.

"Decision to Grant" in EP Application 16733519.9 dated May 23, 2019; 1 page.

* cited by examiner

METHODS FOR MEASURING ANALYTES USING NANOFABRICATED DEVICE

CROSS-REFERENCE TO RELATED APPLICATIONS

This patent application is a continuation of International Patent Application No. PCT/EP2016/065155 filed Jun. 29, 2016, which claims priority to and the benefit of U.S. Provisional Application No. 62/187,161, filed Jun. 30, 2015. Each of the above patent applications is incorporated herein by reference as if set forth in its entirety.

FIELD

This disclosure is generally related to measuring analytes, and more specifically to sequencing linear biomolecules (e.g., DNA, RNA, proteins, and the like) by a nanofabricated device using quantum tunneling effects.

BACKGROUND

In genetics, the term sequencing may refer to methods for determining a primary structure or sequence of a linear biomolecule such as DNA, RNA, amino acids, etc. For example, DNA sequencing is the process of determining an order of nucleobases (adenine, guanine, cytosine and thymine) in a given DNA fragment. DNA sequencing is a powerful method to reveal genetic variations at the molecular level, such as single nucleotide polymorphism, copy number variation, gene fusion, insertion/deletion, etc. It is thus essential to understanding disease mechanisms, genetic diagnosis, and personalized medicine.

DNA sequencing processes typically include extracting and fragmenting target nucleic acids from a sample. The fragmented nucleic acids are used to produce target nucleic acid templates that generally include one or more adapters. The templates can be subjected to amplification methods, such as polymerase chain reaction (PCR), bridge amplification to provide a cluster or rolling circle replication in the form of a nucleic acid "nanoball," also called a DNA nanoball (DNB). Sequencing applications are then performed on the single-stranded nucleic acids, e.g., by sequencing by synthesis or by ligation techniques. Such amplification processes, however, are generally associated with high costs, replicative sequencing being required for high accuracy, short read lengths, and a long turnaround time per run (TTR).

A number of technologies for sequencing DNA at the single-molecule level have been developed in an effort to address the disadvantages of amplification methods. For example, nanopore sequencing exploits changes in ionic current as a nucleobase traverses a tiny channel present in a protein or solid-state material subjected to an applied voltage and immersed in a conductive fluid. Further discussion of nanopore sequencing can be found in Wang et al., The Evolution of Nanopore Sequencing, *Frontiers in Genetics*, 2015, 5, 449, which is incorporated by reference herein for all purposes. Although such single-molecule sequencing methods overcome some of the drawbacks of earlier generation amplification methods, they nevertheless retain certain disadvantages such as low resolution which in turn requires replicative sequencing.

Very recently, devices have been demonstrated for the sequencing of DNA using quantum tunneling current between electrodes. When a DNA segment is present in the space between the electrodes, a change in the quantum tunneling current can be detected. The magnitude of change can be mapped to the particular nucleobase present when the measurement is made. One example of a device that uses quantum tunneling effects to sequence DNA is a Mechanically Controllable Break Junction (MCBJ) device. One such device is shown in FIGS. 1A-1B.

As seen in FIG. 1A, the MCBJ device 100 includes a silicon substrate 102 on which gold electrodes 108, 108' are formed. Substrate 102 is positioned on a probe 104 that contacts the bottom surface of substrate 102 at a contact point 104', and two force members 106 apply a downward force at contact points 106' of the top surface of substrate 102. Prior to applying the force, electrodes 108, 108' are present as a single gold electrode structure. The force creates a strain on the electrode structure, and is gradually increased until the electrode structure fractures to form electrodes 108, 108' separated by a gap 110 shown in the close-up view at the top-center of FIG. 1A. The force applied at contact points 106' can then be increased or relaxed to adjust the size of gap 110 to that required for detecting changes in quantum tunneling current when a DNA fragment is present in gap 110.

FIG. 1B shows a Transmission Electron Microscopy (TEM) image of MCBJ device 100 including silicon substrate 102 and a parallel array of gold electrodes structures. The electrode structures shown in FIG. 1B have not yet been fractured. Upon applying the force at contact points 106' depicted in FIG. 1A, the electrode structures of FIG. 1B will fracture to form electrodes 108, 108' separated by gap 110.

MCBJ device 100 shown in FIGS. 1A-1B can be used to sequence DNA at the single-molecule level by measuring changes in quantum tunneling current across electrodes 108, 108' when a nucleobase is present in gap 110. Device 100, however, is associated with a number of disadvantages. For example, the lateral dimensions of electrodes 108, 108' must be precisely controlled in order to create the width of gap 110 required to observe changes in quantum tunneling current when a nucleobase is present in gap 110. As silicon substrate 102 is flexed after fracture, the spacing between electrodes 108, 108' can be adjusted and thus the width of gap fixed at the appropriate value. None of the other electrodes in the array, however, may have a gap with the precise spacing required. As a result, only a single MCBJ sensor may function on a chip at any specific adjusted gap width. Further, MCBJ device 100 requires the use of gold for electrodes 108, 108'. Due to its high diffusivity in silicon and its tendency to form charge traps, gold is typically forbidden in semiconductor foundries. Thus, fabricating MCBJ device 100 requires specialized manufacturing facilities in addition to non-standard lithography and patterning techniques.

Accordingly, it would be desirable to provide improved devices and methods for sequencing DNA and other linear biomolecules at the single-molecule level.

BRIEF SUMMARY

Embodiments of the invention provide improved devices, methods of making devices, and methods of using devices, for sequencing linear biomolecules at the single-molecule level using quantum tunneling effects. In some embodiments, a nanofabricated device is provided including a substrate, a first electrode disposed on a first portion of a top surface of the substrate, a dielectric layer disposed on as second portion of the top surface of the substrate, and a second electrode disposed on the dielectric layer and suspended over the first electrode. A gap can be defined by a top surface of the first electrode and a bottom surface of the second electrode. The width of the gap can be nanodimensioned (e.g., 0.8 to 5.0 nm) and can correspond to the size of a linear biomolecule (e.g., a DNA, RNA, or protein molecule) such that a quantum tunneling current is transmitted between the electrodes when a voltage is applied across the electrodes (i.e. when the electrodes have different potentials) and a part of the linear molecule (e.g., a nucleobase or amino acid) is present in the gap.

Other embodiments are directed to methods of making a nanofabricated device for sequencing linear biomolecules at the single-molecule level and using quantum tunneling effects. The methods can incorporate deposition techniques such as atomic layer deposition (ALD) to form the highly precise gap width suitable for detecting changes in quantum tunneling current (or voltage) when a nucleobase is present in the gap. ALD can involve sequential application of two gas-phase precursor chemicals onto a substrate. The precursors react with the substrate surface in a sequential, self-limiting manner. By exposing the precursors to the substrate surface repeatedly, a thin film can be deposited. Since the thin film is grown one atom or molecule at a time, the thickness of the film can be precisely controlled. The ALD film can be deposited between two conductive layers patterned to form two electrodes, the spacing between the electrodes being precisely controlled by the thickness of the ALD film. Upon removing the ALD film from the region between the conductive layers, a gap with precise dimensions can be created between the electrodes. Embodiments of the invention can also utilize other deposition techniques such as chemical vapor deposition (CVD), physical vapor deposition (PVD), ion-beam sputtering (IBS), reactive sputtering, and the like to form a sacrificial film that when removed provides the gap of desired width.

Other embodiments are directed to methods of using a nanofabricated device for sequencing linear biomolecules at the single-molecule level and using quantum tunneling effects. As described above, the nanofabricated device can include a precisely formed gap between two electrodes. Although there can be no direct electrical connection between the electrodes, a small amount of current can tunnel from one electrode to the other when a voltage is applied. Linear biomolecules such as DNA, RNA, proteins, and the like are characterized by an impedance. When such a linear molecule passes through the gap, the presence of the biomolecule can affect the amount of the quantum tunneling current. Individual nucleobases (e.g., adenine, guanine, cytosine, and thymine) and amino acids are characterized by different impedance values. Thus, the change in quantum tunneling current can depend on the particular nucleobase or amino acid present in the gap when the measurement is made. As the biomolecule traverses the gap between the electrodes with the precisely defined spacing, the sequential changes in measured tunneling current or voltage can reflect the sequence of the biomolecule.

Some embodiments provide a device for sequencing a linear biomolecule using quantum tunneling, the device comprising: a substrate having a top surface; a first electrode disposed on a first portion of the top surface of the substrate; a first dielectric layer disposed on a second portion of the top surface of the substrate; a second electrode disposed on the first dielectric layer and suspended over the first electrode; and a gap defined by a top surface of the first electrode and a bottom surface of the second electrode, wherein a width of the gap corresponds to a size of the linear biomolecule such that a quantum tunneling current is transmitted between the first electrode and the second electrode when: a voltage is applied across the first electrode and the second electrode; and a part of the linear biomolecule is present in the gap.

In some embodiments, the substrate comprises a second dielectric layer disposed on a semiconductor substrate. In further embodiments, the width of the gap is about 0.8 to 5.0 nm. In some embodiments, the gap is further defined by a top surface of the first dielectric layer and a side surface of the second electrode. In further embodiments, the top surface of the first dielectric layer and the top surface of the first electrode are substantially coplanar. In some embodiments, the first electrode and the second electrode are oriented orthogonally to one another. In further embodiments, the device further comprises circuitry electrically coupled to the first electrode and the second electrode, wherein the circuitry is configured to: apply the voltage across the first electrode and the second electrode; and measure: the quantum tunneling current transmitted between the first electrode and the second electrode; the voltage across the first electrode and the second electrode; or an impedance between the first electrode and the second electrode. In some embodiments, the first electrode and the second electrode individually comprise a material selected from a group consisting of metals, semiconductors, carbon, conductive ceramics, and conductive polymers. In further embodiments, the first dielectric layer comprises a material selected from the group consisting of oxides, dielectric ceramics, polymers, carbonates, glasses, minerals, and air.

Other embodiments provide a method of making a device for sequencing a linear biomolecule using quantum tunneling, the method comprising: providing a substrate having a top surface; depositing a first electrode onto a first portion of the top surface of the substrate; depositing a first dielectric layer onto a second portion of the top surface of the substrate; depositing a sacrificial layer onto a top surface of the first electrode; depositing a second electrode onto the sacrificial layer and onto a top surface of the first dielectric layer; and removing the sacrificial layer, thereby forming a gap defined by the top surface of the first electrode and a bottom surface of the second electrode, wherein a width of the gap corresponds to a size of the linear biomolecule such that a quantum tunneling current is transmitted between the first electrode and the second electrode when: a voltage is applied across the first electrode and the second electrode; and a part of the linear biomolecule is present in the gap.

In some embodiments, the substrate comprises a second dielectric layer disposed on a semiconductor substrate. In further embodiments, the width of the gap is about 0.8 to 5.0 nm. In some embodiments, the sacrificial layer is further deposited onto the top surface of the first dielectric layer, wherein the gap is further defined by the top surface of the first dielectric layer and a side surface of the second electrode. In further embodiments, the top surface of the first dielectric layer and the top surface of the first electrode are substantially coplanar. In some embodiments, the first electrode and the second electrode are oriented orthogonally to one another. In further embodiments, the sacrificial layer is deposited using an atomic layer deposition process. In some embodiments, the sacrificial layer is removed using an etching process, wherein the etching process includes exposing the sacrificial layer to an etchant. In further embodiments, the sacrificial layer comprises a material selected from the group consisting of metals, oxides, nitrides, and carbon containing materials. In some embodiments, the etchant comprises a substance selected from the group consisting of hydrofluoric acid, phosphoric acid, hydrochloric acid, nitric acid, sodium hydroxide, SC-1 solution, organic solvents, and $O_2$ plasma. In further embodiments, the method further comprises electrically coupling circuitry to the first electrode and the second electrode, wherein the circuitry is configured to: apply the voltage across the first electrode and the second electrode; and measure: the quantum tunneling current transmitted between the first electrode and the second electrode; the voltage across the first electrode and the second electrode; or an impedance between the first electrode and the second electrode. In some embodiments, the first electrode and the second electrode individually comprise a material selected from the group consisting of metals, semiconductors, carbon, conductive ceramics, and conductive polymers. In further embodiments, the first dielectric layer comprises a material selected from the group consisting of oxides, dielectric ceramics, polymers, carbonates, glasses, minerals, and air.

Other embodiments provide a method of using a device for sequencing a linear biomolecule using quantum tunneling, the method comprising: providing the device comprising: a substrate having a top surface; a first electrode disposed on a first portion of the top surface of the substrate; a first dielectric layer disposed on a second portion of the top surface of the substrate; a second electrode disposed on the first dielectric layer and suspended over the first electrode; a gap defined by a top surface of the first electrode and a bottom surface of the second electrode; and circuitry electrically coupled to the first electrode and the second electrode; applying, using the circuitry, a voltage across the first electrode and the second electrode; introducing a part of the linear biomolecule into the gap; measuring, using the circuitry: a quantum tunneling current transmitted between the first electrode and the second electrode; the voltage across the first electrode and the second electrode; or an impedance between the first electrode and the second electrode; and identifying, based on the measured quantum tunneling current, the measured voltage, or the measured impedance, the part of the linear biomolecule introduced into the gap.

In some embodiments, the linear biomolecule is selected from the group consisting of DNA, RNA, polypeptides, and proteins. In further embodiments, the part of the linear biomolecule comprises a nucleobase or an amino acid. In some embodiments, the substrate comprises a second dielectric layer disposed on a semiconductor substrate. In further embodiments, a width of the gap is about 0.8 to 5.0 nm. In some embodiments, the gap is further defined by a top surface of the first dielectric layer and a side surface of the second electrode, wherein the top surface of the first dielectric layer and the top surface of the first electrode are substantially coplanar, and wherein the first electrode and the second electrode are oriented orthogonally to one another. In further embodiments, the first electrode and the second electrode individually comprise a material selected from the group consisting of metals, semiconductors, carbon, conductive ceramics, and conductive polymers. In some embodiments, the first dielectric layer comprises a material selected from the group consisting of oxides, dielectric ceramics, polymers, carbonates, glasses, minerals, and air.

A better understanding of the nature and advantages of embodiments of the present invention may be gained with reference to the following detailed description and the accompanying drawings.

DEFINITIONS

Figure 1A:
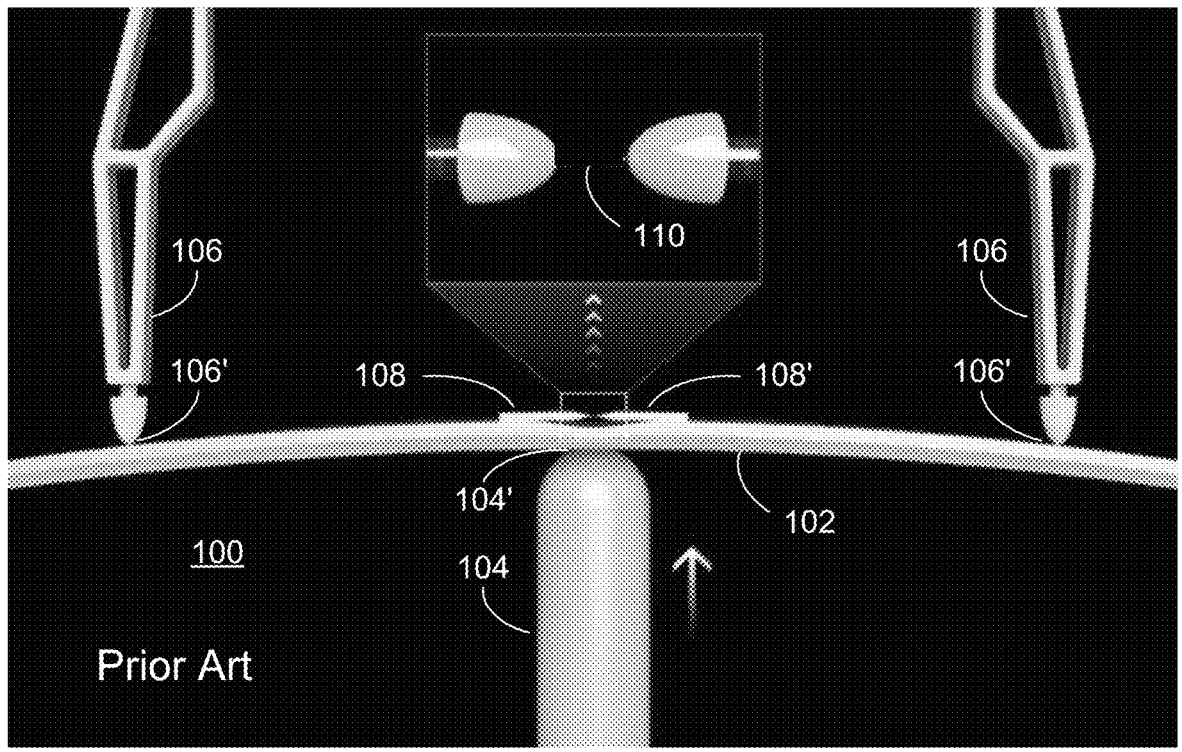
FIG. 1A shows a schematic of an existing MCBJ device used to sequence DNA by measuring quantum tunneling current across a break junction formed between gold electrodes.
Figure 1B:
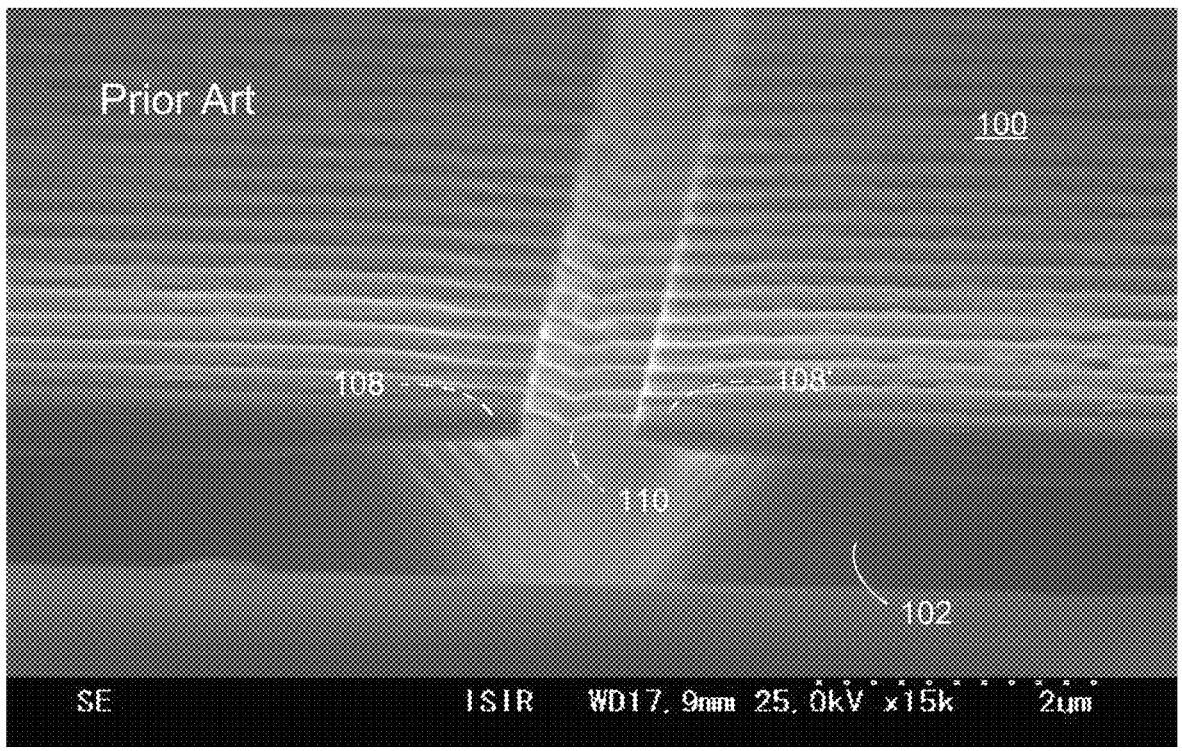
FIG. 1B shows a TEM image of the MCBJ depicted in FIG. 1A including the gold electrode structure prior to forming the break junction.

The following definitions may be helpful in providing background for an understanding of embodiments of the invention.

A "linear biomolecule" refers to a type of molecule that is present in a living organism in the form of polymers containing monomeric units that are covalently bonded to form larger chain-like structure. Exemplary linear biomolecules include, but are not limited to, polynucleotides (e.g., DNA and RNA), polypeptides, and proteins. In some embodiments, linear biomolecules can also include branched or cyclic biomolecules including one or more linear portions.

A "part of a linear molecule" refers to a monomer of a linear biomolecule. Exemplary parts of linear biomolecules include, but are not limited to, nucleobases and amino acids.

A "nucleobase" refers to nitrogen-containing organic molecules that serve as the monomers of polynucleotides such as DNA and RNA. Exemplary nucleobases include, but are not limited to, cytosine, guanine, adenine, thymine, and uracil.

An "amino acid" refers to organic compounds comprising amine and carboxylic acid groups, and a side-chain, and that serve as the monomers of polypeptides and proteins.

"Quantum tunneling" refers to the quantum mechanical phenomenon where a particle tunnels through an energy barrier that classical (i.e. Newtonian) mechanics conclude could not be overcome by the particle. In the case of electrons tunneling through an energy barrier between two electrodes, such tunneling is referred to as "quantum tunneling current."

An "electrode" refers to a circuit element comprising an electrically conducting material and that makes contact with a nonmetallic part of a circuit such as air or vacuum. Suitable electrically conductive materials include, but are not limited to, metals, semiconductors, carbon, conductive ceramics, and conductive polymers.

A "dielectric layer" refers to a layer comprising an insulator material that is a poor electrical conductor. Exemplary dielectric materials include, but are not limited to, oxides, dielectric ceramics, polymers, carbonates, glasses, mineral, and air.

"Atomic layer deposition" refers to a thin film deposition technique where one or more precursors in the gas phase react with the surface of a substrate in a self-limiting manner such that the reaction terminates once all reactive sites on the surface are consumed. In some embodiments, atomic layer deposition can involve exposing a substrate to two gas phase precursors in a sequential manner In some other embodiments, atomic layer deposition can involve depositing a thin film by way of a single precursor using, for example, plasma or radical enhanced processes.

A "sacrificial layer" refers to a formed layer of material that is subsequently removed by a process such as etching. Exemplary sacrificial layer materials include, but are not limited to, metals, oxides, nitrides, and carbon containing materials.

"Etching" refers to the process of using a corrosive substance (i.e. an etchant) to dissolve a solid material. Exemplary etchants include, but are not limited to, hydrofluoric acid, phosphoric acid, hydrochloric acid, nitric acid, sodium hydroxide, SC-1 solution, organic solvents, and etching by plasmas. Plasma etching can involve a stream of glow discharge (plasma) of an appropriate gas mixture. The plasma source, known as etch species, can be either charged (ions) or neutral (atoms and radicals) created in a vacuum system by way of radio frequency or microwave excitations. "Selective etching" refers to the process of selecting and using a particular etchant that dissolves a first solid material but does not dissolve a second solid material that may be adjacent to the first solid material.

"Circuitry" refers to an electronic circuit or system of electronic circuits that perform one or more functions in an electronic device. Electronic circuits can include electronic components such as resistors, transistors, capacitors, inductors, and diodes, connected by conductive wires or traces through which electrical current can flow. Circuitry can include one or more integrated circuits and, in some embodiments, can include software executed by one or more integrated circuits.

DETAILED DESCRIPTION

Embodiments can provide improved devices, methods of making devices, and methods of using devices, for sequencing linear biomolecules at the single-molecule level using quantum tunneling effects. In some embodiments, a nanofabricated device is provided including a precisely formed gap disposed between two electrodes and having a very small width (e.g., 0.8 to 5.0 nm). The width of the gap can correspond to the size of a linear biomolecule such as DNA, RNA, a polypeptide, a protein, and the like. When a part of the linear biomolecule (e.g., a nucleobase or amino acid) is present in the gap and a voltage is applied across the electrodes, a change in quantum tunneling current (or voltage) can be measured. The magnitude of the change can be mapped to the particular biomolecule part present at the time of measurement. As the linear biomolecule (or molecular fragment) traverses the gap, sequencing can be performed by taking subsequent measurements at time intervals selected based upon the biomolecule's traversal velocity.

The precisely dimensioned gap can be formed by depositing a thin film between two electrodes using a deposition process such as ALD. The sacrificial film can then be removed by way of selective etching, with the resulting void forming the gap. Since processes such as ALD can deposit layers of a desired material having the thickness of a single atom or molecule, film thickness can be accurately controlled, thereby resulting in a quantum tunneling gap engineered to having the desired width at a very high level of precision. Moreover, by using deposition processes to form the nanofabricated devices of the present invention, many detectors can be placed on a single integrated circuit chip. Due to the large number of nucleobases in a DNA or RNA molecule, for example, sequencing can be performed at a rapid pace as many fragments can be sequenced simultaneously.

Further, methods of the present invention for making nanofabricated devices can be performed using generally available semiconductor processing equipment and using materials commonly used in semiconductor foundries. Some semiconductor foundries forbid the use of gold and certain other transitional metals that can act as charge recombination centers. Such metals show high diffusivity in silicon, and thus contamination on a wafer surface can lead to charge traps being formed in depletion regions of the p-n junctions during thermal processing. Although embodiments of the present invention can utilize gold as an electrode material (i.e. as done in existing MCBJ devices), materials other than gold and charge trap-forming transition metals can be used. In some embodiments, methods of the present invention can also use existing semiconductor fabrication techniques (e.g., deposition, photolithography, etching, and the like) to form the nanofabricated devices. By using processing equipment, techniques, and materials compatible with existing semiconductor fabrication, the nanofabricated devices of the present invention can be made in a more time efficient and cost-effective manner as compared to existing single-molecule sequencing devices.

I. Nanofabricated Device

Figure 2A:
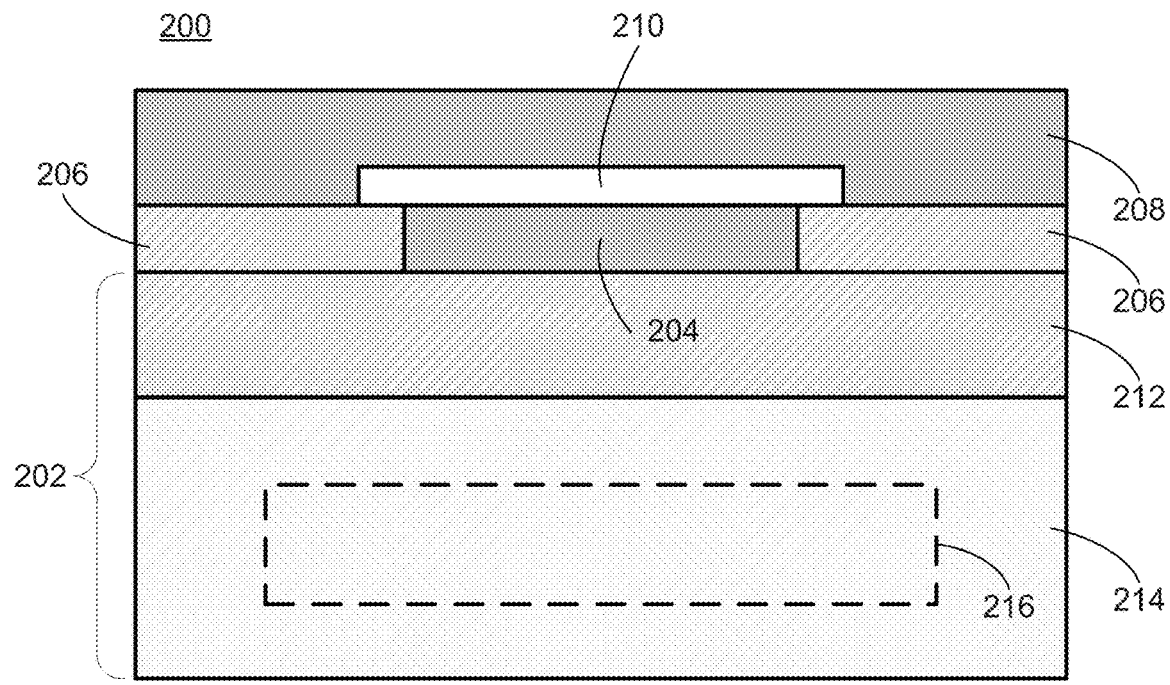
FIG. 2A shows a schematic cross-sectional side view of a nanofabricated device for sequencing linear biomolecules using quantum tunneling according to embodiments of the present invention.
Figure 2B:
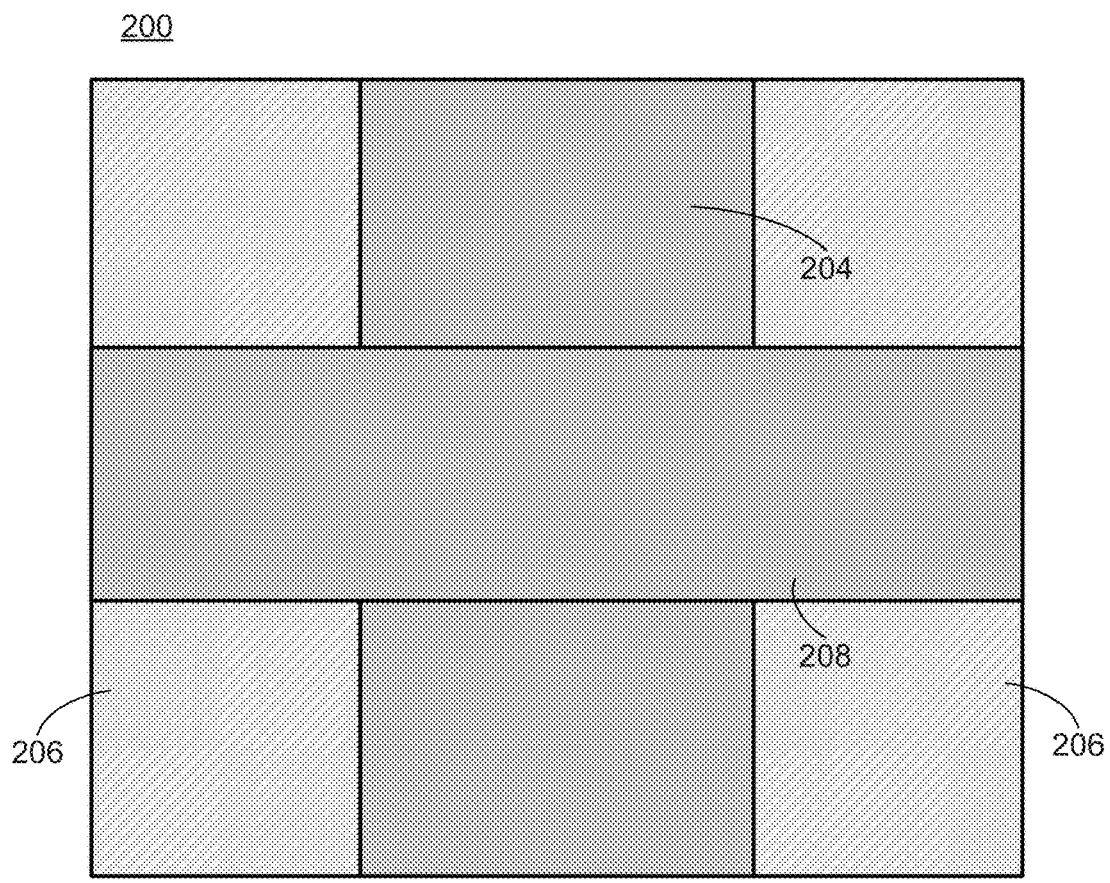
FIG. 2B shows a schematic top view of a nanofabricated device for sequencing linear biomolecules using quantum tunneling according to embodiments of the present invention.

FIGS. 2A-2B show schematics of a nanofabricated device 200 for sequencing linear biomolecules using quantum tunneling according to embodiments of the present invention. FIG. 2A shows a cross-sectional side view of device 200, and FIG. 2B shows a top view of device 200. It should be noted that the schematics of device 200 shown in FIGS. 2A-2B are merely one possible configuration, and that one of skill in the art will appreciate that embodiments of the present invention encompass other configurations.

As shown in FIG. 2A, device 200 can include a substrate 202 having a top surface, a first electrode 204 disposed on a first portion of the top surface of substrate 202, a first dielectric layer 206 disposed on a second portion of the top surface of substrate 202, and a second electrode 208 disposed on first dielectric layer 206 and suspended over first electrode 204. As shown in FIG. 2A, device 200 can include a gap 210 defined by a top surface of first electrode 204 and a bottom surface of second electrode 208. The width of gap 210 (i.e. the distance between the top surface of first electrode 204 and the bottom surface of second electrode 208) can correspond to a size of a linear biomolecule such that a quantum tunneling current is transmitted between first electrode 204 and second electrode 208 when a voltage is applied across first electrode 204 and second electrode 208 and a part of the linear biomolecule is present in gap 210.

As described in further detail below, the width of gap 210 can be precisely dimensioned using a deposition process such as ALD to form a sacrificial layer between first electrode 204 and second electrode 208. The sacrificial layer can be subsequently removed (e.g., via selective etching) to form gap 210. The width of gap 210 can be dimensioned to correspond to the size of the type of linear biomolecule to be sequenced using device 200. In some embodiments, the width of gap 210 can be about 0.8 to 5.0 nm. When device 200 is used to sequence small linear biomolecules such as DNA or RNA, the width of gap 210 can be about 0.8 to 1.2 nm in some embodiments. For larger biomolecules such as polypeptides or proteins, the width of gap 210 can be about 1.2 to 5.0 nm in some embodiments.

The width of gap 210 can be adjustable in some embodiments. For example, first dielectric layer 206 can include (or be replaced by) a piezoelectric element comprising a material that expands in volume in response to an applied electromagnetic field. As shown in FIG. 2A, in this non-limiting example, an expansion of the piezoelectric element in the vertical direction can cause second electrode 208 to move in the vertical direction, thereby increasing the width of gap 210.

In some embodiments, as shown in FIG. 2A, gap 210 can be further defined by a top surface of first dielectric layer 206 and a side surface of second electrode 208. In such embodiments, the top surface of first dielectric layer 206 and the top surface of first electrode 204 can be substantially coplanar. In some other embodiments, first electrode 204 can be recessed such that its top surface is in a plane below that formed by the top surface of first dielectric layer 206. In such embodiments, gap 210 can be further defined by a side surface of first dielectric layer 206.

First electrode 204 and second electrode 208 can each comprise any suitable electrically conductive material, including but not limited to, metals, semiconductors, carbon, conductive ceramics, and conductive polymers. Exemplary metals can include Cu, W, Ti, Au, Ag, Al, Zn, Ni, Fe, Pt, Ta, and the like. Exemplary semiconductors can include Si, Ge, SiGe, GaAs, InP, and the like. Exemplary carbon allotropes and morphologies can include diamond, graphite, graphene, nanotubes, nanofibers, vapor grown carbon fiber (VGCF), and the like. In some embodiments, carbon-containing compounds can be used as the material for first electrode 204 and second electrode 208. Exemplary conductive ceramics can include TiN, TaN, indium tin oxide (ITO), lanthanum-doped strontium titanate (SLT), yttrium-doped strontium titanate (SYT), and the like. Exemplary conductive polymers can include poly(pyrrole)s (PPY), polyanilines (PANI), poly(thiophene)s (PT), poly(3,4-ethylenedioxythiophene) (PEDOT), poly(p-phenyl sulfide) (PPS), poly(acetylene)s (PAC), poly(p-phenylene vinylene) (PPV), and the like.

In some embodiments, first electrode 204 and second electrode 208 can comprise the same electrically conductive material. In other embodiments, first electrode 204 and second electrode 208 can comprise different electrically conductive materials.

First dielectric layer 206 can comprise any suitable electrically insulating material including, but not limited to, oxides, dielectric ceramics, polymers, carbonates, glasses, minerals, and air. Exemplary oxides can include $SiO_2$, $Si_2O_3$, $Al_2O_3$, $ZrO_2$, $Fe_2O_3$, MgO, ZnO, $Ta_2O_5$, $HfO_2$, titanates, and the like. Exemplary dielectric ceramics can include $Si_3N_4$, SiC, SiAlON, AlN, and the like. Exemplary polymers can include paralene, photopolymers (e.g., photoresists), hydrocarbon rubbers (e.g., EPM, EPDM, and the like), nitriles, polyethylenes, polyurethanes, silicones, and the like. Exemplary carbonates can include $CaCO_3$, $MgCO_3$, and the like. Exemplary glasses can include borosilicate glass, soda-lime glass, and the like. Exemplary minerals can include mica, steatite, cordierite, and the like.

As shown in FIG. 2A, in some embodiments, substrate 202 can include a second dielectric layer 212 disposed on a semiconductor substrate 214. Second dielectric layer 212 can comprise any suitable electrically insulating material described above with respect to first dielectric layer 206. In some embodiments, first dielectric layer 206 and second dielectric layer 212 can comprise the same electrically insulating material. In other embodiments, first dielectric layer 206 and second dielectric layer 212 can comprise different electrically insulating materials. In FIG. 2A, first dielectric layer 206 and second dielectric layer 212 are depicted as two separate layers. In some embodiments, first dielectric layer 206 and second dielectric layer 212 in combination can be a single layer of electrically insulating material.

Semiconductor substrate 214 can comprise any suitable semiconducting material including, but not limited to, Si, Ge, SiGe, GaAs, InP, and the like. In some embodiments, semiconductor substrate 214 can be an integrated circuit chip comprising circuitry 216 which can be electrically coupled to first electrode 204 and second electrode 208. For example, in some embodiments, circuitry 216 can be electrically coupled to first electrode 204 using a first via through second dielectric layer 212, and circuitry 216 can be electrically coupled to second electrode 208 using a second via through second dielectric layer 212 and first dielectric layer 206. Circuitry 216 can be configured to apply a voltage across first electrode 204 and second electrode 208, and measure quantum tunneling current transmitted between (or the voltage across) first electrode 204 and second electrode 208.

As described herein, when a part of a linear biomolecule is present in gap 210 and a voltage is applied across first electrode 204 and second electrode 208, a quantum tunneling current can be transmitted between first electrode 204 and second electrode 208. The measured quantum tunneling current (or resulting voltage) can be mapped to the particular part of the biomolecule present in gap 210, and sequencing can be accomplished by repeating the measurements as the biomolecule traverses gap 210. Circuitry 216 can be configured to perform such mapping operations or, alternatively, can transmit current or voltage measurements to an external computing device configured to perform some or all of the mapping operations.

In FIG. 2A, circuitry 216 is depicted as being contained within semiconductor substrate 214 of device 200. In other embodiments, all or a portion of circuitry 216 can be present outside substrate 202. For example, one or more transistors, capacitors, resistors, diodes, and/or inductors of circuitry 216 can reside external to substrate 202 or external to device 200 altogether. For example, in some embodiments, all or a portion of circuitry 216 can be in the form of an external integrated circuit chip or in any other suitable configuration external to device 200.

FIG. 2B shows a schematic top view of device 200 including first electrode 204, first dielectric layer 206, and second electrode 208. As depicted in FIG. 2B, first electrode 204 and second electrode 208 can be oriented orthogonally to one another. This, however, is not intended to be limiting. In other embodiments, first electrode 204 and second electrode 208 can be oriented parallel to one another or at any suitable angle between 0 and 180° so long as gap 210 is present between first electrode 204 and second electrode 208.

Device 200 can be one of many devices on a single integrated circuit chip. For example, the top surface of semiconductor substrate 214 can be large enough to support an array of many devices each including first dielectric layer 206, second dielectric layer 212, first electrode 204, second electrode 208, and gap 210. In some embodiments, each device can be separated by a dielectric layer to prevent electrodes in adjacent devices from coming into electrical or physical contact with one another. In some embodiments, each device in an array can include its own circuitry (e.g., circuitry 216) for applying voltages and measuring quantum tunneling current or voltage generated within the specific device (i.e. device 200). In some other embodiments, the circuitry for multiple devices can be integrated such that circuitry 216 applies voltages and measures quantum tunneling currents or voltages when linear biomolecules are present in the gaps of some or all of the devices in the array.

By providing multiple devices on a single integrated circuit chip, many biomolecule fragments can be sequenced simultaneously since quantum tunneling current and voltage measurements can be made as the fragments traverse the gaps of each device in the array. As a result, linear biomolecules can be sequenced at the single-molecule level with improved speed and efficiency.

II. Method of Making Nanofabricated Device

Embodiments of the invention also provide methods of making a nanofabricated device for sequencing linear biomolecules at the single-molecule level and using quantum tunneling effects. In such methods, generally available semiconductor processing equipment and materials compatible with existing semiconductor fabrication processes can be used. Moreover, existing semiconductor fabrication techniques (e.g., photolithography, etching, deposition, and the like) can be used to form the nanofabricated devices. As a result, the nanofabricated devices of the present invention can be made in a more time efficient and cost-effective manner as compared to existing single-molecule sequencing devices.

A. Semiconductor Manufacturing Processes

Embodiments of the invention provide methods of making nanofabricated devices using, at least in part, existing semiconductor fabrication techniques such as photolithography, electron-beam (e-beam) lithography, etching, deposition, and the like.

Photolithography is used in the semiconductor industry to pattern solid materials such as semiconductor (e.g., Si) wafers. The technique uses light to transfer a geometric pattern from a photomask to a light-sensitive chemical called a "photoresist" disposed on the material surface. The photomask can be an opaque plate including transparent regions that allow light to shine through in the particular geometric pattern. Subsequent chemical treatments can be used to engrave the exposure pattern into the material underneath the photoresist, and such treatments can also be used to allow a new material to be deposited in the geometric pattern. Several photolithography cycles can be performed to fabricate a material having the desired microstructure, with each iteration involving several steps performed sequentially.

In an exemplary photolithography process, the starting material is initially cleaned using a wet chemical treatment (e.g., hydrogen peroxide, trichloroethylene, acetone, methanol, or the like) to remove surface contaminants. The material is then heated to evaporate any moisture on the surface, and a chemical such as bis(trimethylsilyl)amine is applied to promote adhesion of the photoresist to the material surface. Using a spin coating process, a liquid photoresist solution is then applied to the material to form a coating having a uniform thickness of, for example, about 3 microns or less. Exemplary photoresists can include, but are not limited to, poly(methyl methacrylate) (PMMA), poly(methyl glutarimide) (PMGI), phenol formaldehyde resin, SU-8, and the like. The coated material is then prebaked to evaporate any excess photoresist solution.

The photoresist coated material is subjected to a pattern of intense UV or X-ray light which causes a chemical change in the photoresist layer that allows the photoresist material to be removed using a developer solution such as tetramethylammonium hydroxide (TMAH). If a "positive" photoresist is used, the regions exposed to the UV (or X-ray) light can dissolve in the developer solution. Alternatively, in the case of a "negative photoresist," the non-exposed regions of the photoresist can dissolve in the developer solution. After a post-exposure bake (PEB), the developer solution is applied followed by a "hard-baking" to solidify the photoresist pattern remaining on the surface of the material.

An etching process can then be used to remove the regions of material not coated with the photoresist, thereby forming the desired geometric pattern in the material. This can be accomplished using a liquid etchant (e.g., hydrofluoric acid, phosphoric acid, hydrochloric acid, nitric acid, sodium hydroxide, SC-1 solution, organic solvents, and the like) or a plasma etchant (e.g., oxygen, argon, and the like). The photoresist can then be removed using a liquid resist stripper such as 1-Methyl-2-pyrrolidon (NMP) or a plasma (e.g., containing oxygen).

Other techniques such as e-beam lithography are also used in the semiconductor industry to pattern solid materials. E-beam lithography is a process very similar to photolithography as described above, except that e-beam lithography uses a beam of electrons (instead of light) to transfer a geometric pattern by selectively modifying the solubility of an electron-sensitive resist layer disposed on the material surface. E-beam lithography can be used to transfer geometric patterns at a very small scale (e.g., 10 nm or less).

The photolithography and e-beam lithography techniques described above can be used in some embodiments of the invention to remove regions of material during fabrication of a nanofabricated device for sequencing linear biomolecules. In some embodiments, deposition techniques used in the semiconductor industry can be used to add regions of material when forming the nanofabricated devices described herein. For example, deposition techniques can be used to deposit material into a cavity or void formed by regions of material being removed during photolithography followed by etching processes. Such deposition techniques can include, but are not limited to, atomic layer deposition (ALD), chemical vapor deposition (CVD), physical vapor deposition (PVD), ion-beam sputtering (IBS), and reactive sputtering.

ALD involves deposition of a thin film by causing one or more precursors to react with the surface of a substrate in a self-limiting manner, the resulting film being grown one atomic (or molecular) layer at a time with each iteration. CVD refers to a process where a substrate is exposed to one or more volatile precursors which react or decompose on the substrate surface, thereby forming a deposited layer of material. Any volatile byproducts can be transported out of the CVD reaction vessel using a gas flow. In PVD, a thin film is deposited onto a substrate by condensing the target film material from its vapor phase. IBS involves generating ions of a source material by colliding the material with electrons confined by a magnetic field in a vacuum chamber. An electric field accelerates the ions towards a substrate, with the ions being neutralized by electrons from an external filament prior to striking the substrate and forming the layer of desired material. Reactive sputtering is similar to IBS, with a difference being that a reactive gas (e.g., oxygen, nitrogen, $CO_2$, $C_2H_2$, or $CH_4$) is introduced into the vacuum chamber, the gas reacting with the source material ions to form layers on the substrate comprising, for example, oxides, nitrides, metal-DLCs, carbides, or carbo-nitrides.

B. Method of Making a Nanofabricated Device

FIGS. 3A-3H illustrate a method of making a nanofabricated device for sequencing a linear biomolecule using quantum tunneling according to embodiments of the present invention. The method can utilize photolithography, etching, and deposition techniques used in existing semiconductor fabrication processes to form a layered device including two electrodes separated by a gap. The gap can have a width that corresponds to the size of a linear biomolecule (e.g., DNA, RNA, polypeptide, protein, or the like) to be sequenced, such that a quantum tunneling current is transmitted between the electrodes when a part (e.g., a nucleobase or amino acid) is present in the gap. It should be noted that the method and resulting device depicted in FIGS. 3A-3H are merely one example, and that one of skill in the art will appreciate that embodiments of the present invention encompass modifications to the described method leading to structural modifications to the resulting device.

Figure 3A:
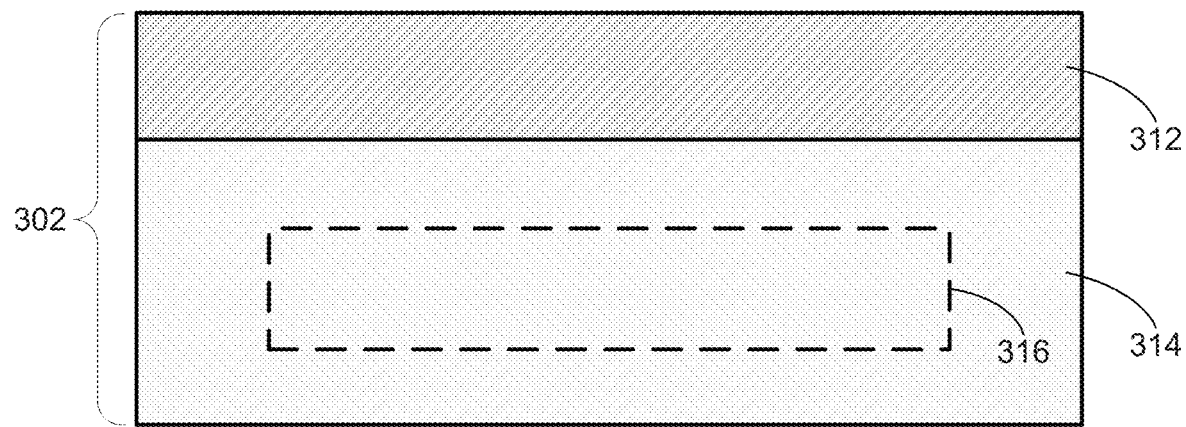
FIGS. 3A-3H illustrate a method of making a device for sequencing a linear biomolecule using quantum tunneling according to embodiments of the present invention.
Figure 3B:
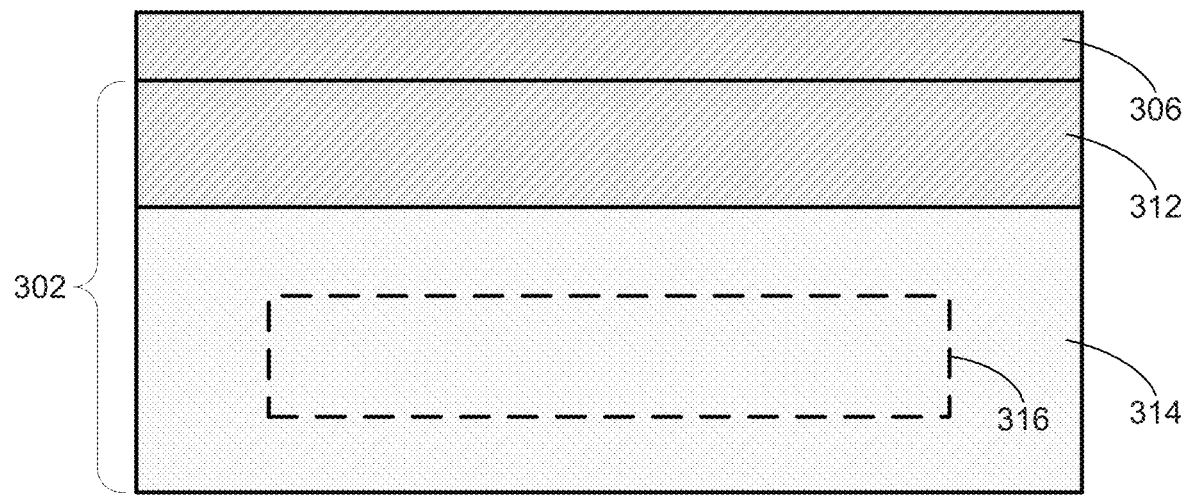

As shown in FIG. 3A, the method can begin by providing a substrate 302 having a top surface onto which a first dielectric layer 306 can be deposited as shown in FIG. 3B. First dielectric layer 306 can be deposited using any suitable deposition technique described herein.

First dielectric layer 306 can comprise any suitable electrically insulating material including, but not limited to, oxides, dielectric ceramics, polymers, carbonates, glasses, minerals, and air. Exemplary oxides can include $SiO_2$, $Si_2O_3$, $Al_2O_3$, $ZrO_2$, $Fe_2O_3$, MgO, ZnO, $Ta_2O_5$, $HfO_2$, titanates, and the like. Exemplary dielectric ceramics can include $Si_3N_4$, SiC, SiAlON, AlN, and the like. Exemplary polymers can include hydrocarbon rubbers (e.g., EPM, EPDM, and the like), nitriles, polyethylenes, polyurethanes, silicones, and the like. Exemplary carbonates an include $CaCO_3$, $MgCO_3$, and the like. Exemplary glasses can include soda-lime glass and the like. Exemplary minerals can include mica, steatite, cordierite, and the like.

In some embodiments, as shown in FIGS. 3A-3B, substrate 302 can include a second dielectric layer 312 disposed on a semiconductor substrate 314. Second dielectric layer 312 can comprise any suitable electrically insulating material described above with respect to first dielectric layer 306. In some embodiments, first dielectric layer 306 and second dielectric layer 312 can comprise the same electrically insulating material. In other embodiments, first dielectric layer 306 and second dielectric layer 312 can comprise different electrically insulating materials.

In FIGS. 3A-3B, first dielectric layer 306 and second dielectric layer 312 are depicted as two separate layers. In such embodiments, substrate 302 can be formed by depositing second dielectric layer 312 onto semiconductor substrate 314 using any suitable deposition technique described herein, with the top surface of substrate 302 being the top surface of second dielectric layer 312. In some other embodiments, first dielectric layer 306 and second dielectric layer 312 in combination can be a single layer of electrically insulating material. For example, a single dielectric layer having the combined thickness of first dielectric layer 306 and second dielectric layer 312 shown in FIGS. 3A-3B can be deposited onto the top surface of semiconductor substrate 314.

Semiconductor substrate 314 can comprise any suitable semiconducting material including, but not limited to, Si, Ge, SiGe, GaAs, InP, and the like. In some embodiments, semiconductor substrate 314 can be an integrated circuit chip comprising circuitry 316 which can be formed within semiconductor substrate 314 before, after, or during fabrication of the nanofabricated device according to various embodiments of the invention.

Figure 3C:
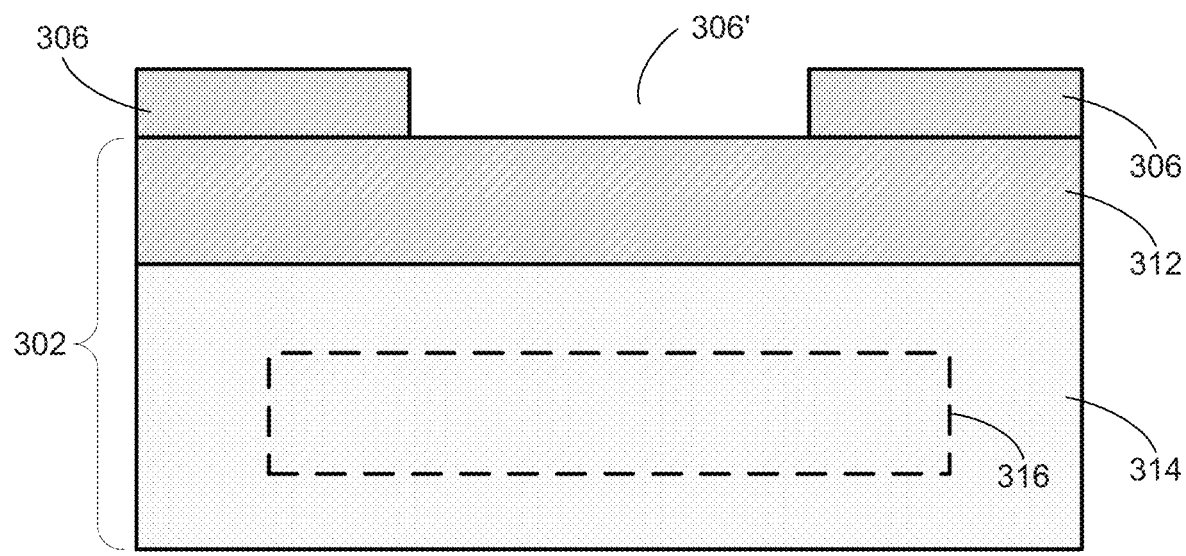

In FIG. 3C, a cavity 306' can be formed by removing a region of first dielectric layer 306. In some embodiments, cavity 306' can be formed using a photolithography process where a photoresist layer is applied to the top surface first dielectric layer 306 shown in FIG. 3B. The photoresist coated surface can then be exposed to UV light in the desired geometric pattern such that a region of the photoresist is dissolved when placed in contact with a developer solution. An etchant can then be used to selectively etch away the region of first dielectric layer 306 to form cavity 306' while preserving the adjacent regions of first dielectric layer 306 protected by the photoresist.

Figure 3D:
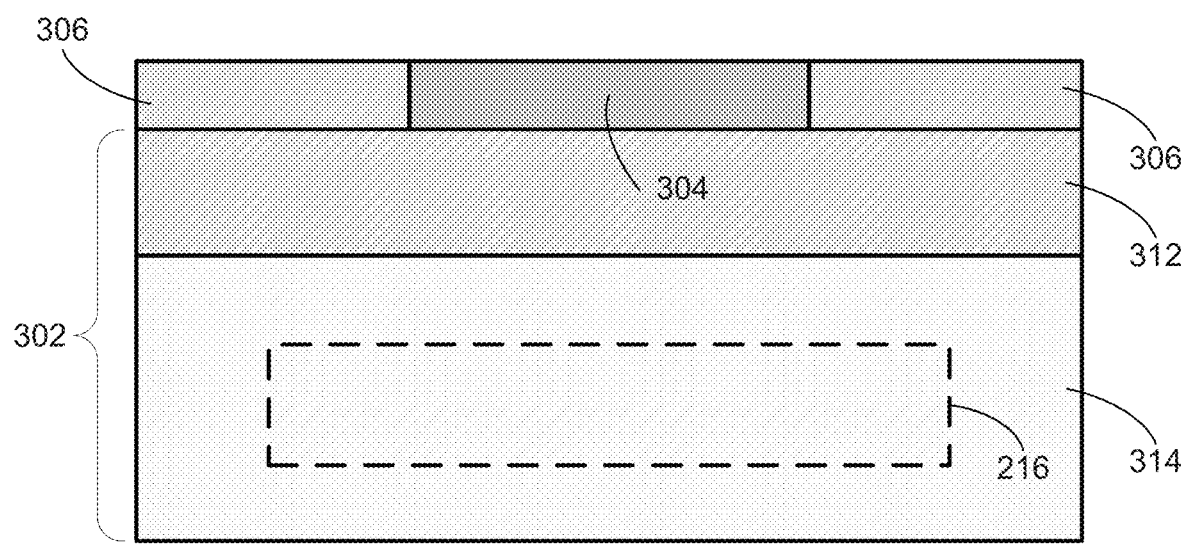

As shown in FIG. 3D, a first electrode 304 can be deposited onto the top surface of substrate 302 and in cavity 306' formed in first dielectric layer 306. First electrode 304 can be deposited using any suitable deposition technique described herein. The resulting structure, as shown in FIG. 3D, can include first electrode 304 being disposed on a first portion of the top surface of substrate 302, and first dielectric layer 306 being disposed on a second portion of the top surface of substrate 302.

First electrode 304 can comprise any suitable electrically conductive material, including but not limited to, metals, semiconductors, carbon, conductive ceramics, and conductive polymers. Exemplary metals can include Cu, W, Ti, Au, Ag, Al, Zn, Ni, Fe, Pt, Ta, and the like. Exemplary semiconductors can include Si, Ge, SiGe, GaAs, InP, and the like. Exemplary carbon allotropes and morphologies can include diamond, graphite, graphene, nanotubes, nanofibers, vapor grown carbon fiber (VGCF), and the like. In some embodiments, carbon-containing compounds can be used as the material for first electrode 204 and second electrode 208. Exemplary conductive ceramics can include TiN, indium tin oxide (ITO), lanthanum-doped strontium titanate (SLT), yttrium-doped strontium titanate (SYT), and the like. Exemplary conductive polymers can include poly(pyrrole)s (PPY), polyanilines (PANI), poly(thiophene)s (PT), poly(3, 4-ethylenedioxythiophene) (PEDOT), poly(p-phenyl sulfide) (PPS), poly(acetylene)s (PAC), poly(p-phenylene vinylene) (PPV), and the like.

In some embodiments, after forming first electrode 304 within cavity 306', the photoresist remaining on the top surface of first dielectric layer 306 can be removed using a liquid resist or plasma stripper. In some other embodiments, the remaining photoresist can be stripped away prior to forming first electrode 304 within cavity 306'. Further, in some embodiments, the top surface of first electrode 304 can be planarized using, for example, a chemical mechanical polishing (CMP) process. In the configuration shown in FIG. 3D, the top surface of first dielectric layer 306 can also be planarized by way of CMP or other process such that the top surfaces of first dielectric layer 306 and first electrode 304 are substantially coplanar. In some other embodiments, first electrode 304 can be deposited onto first dielectric layer 306 and within cavity 306'. A CMP process can then be used to remove the portions of first electrode 304 deposited onto first dielectric layer 306 and to cause the top surfaces of first dielectric layer 306 and first electrode 304 to be substantially coplanar. Such a process may be similar to an "additive patterning" or "Damascene" technique where a material is patterned using CMP as opposed to etching.

Figure 3E:
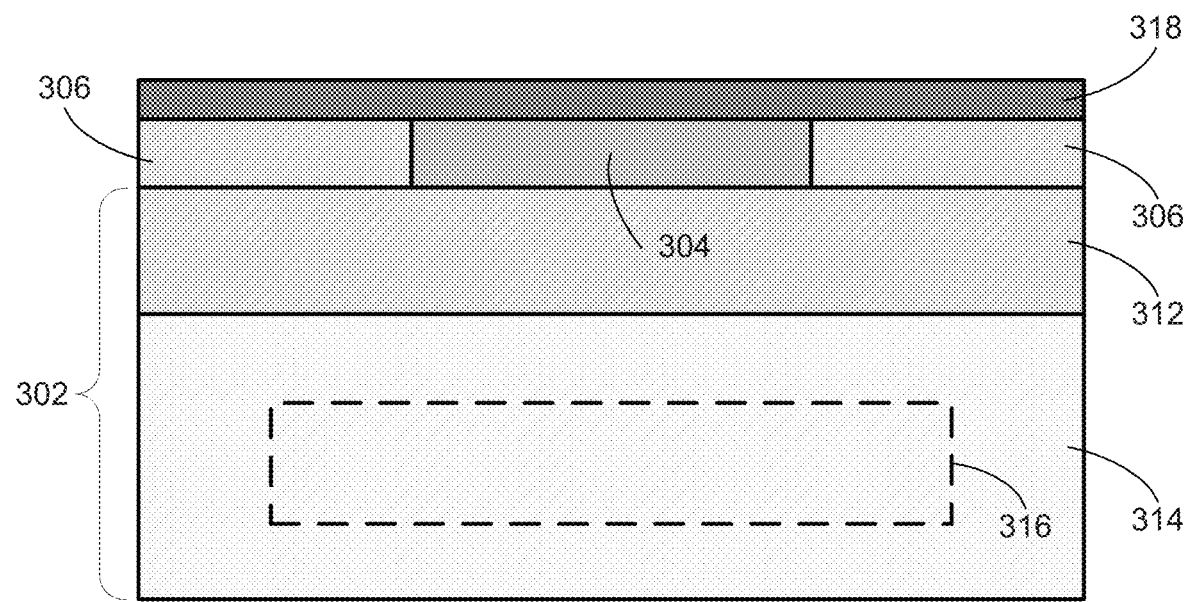

As shown in FIG. 3E, a sacrificial layer 318 can then be deposited onto a top surface of first electrode 304. Sacrificial layer 318 can be deposited using any suitable deposition technique described herein. For example, in some embodiments, sacrificial layer can be deposited using ALD to form a thin film having a thickness of about 0.8 to 5.0 nm. As described in further detail below, sacrificial layer 318 can comprise any suitable material characterized by a different etch rate with respect to the other materials used in the device. For example, sacrificial layer 318 can comprise any suitable metal, oxide, nitride, or carbon-containing material described herein. In some embodiments, the top surface of sacrificial layer 318 can be planarized using, for example, a chemical mechanical polishing (CMP) process.

Figure 3F:
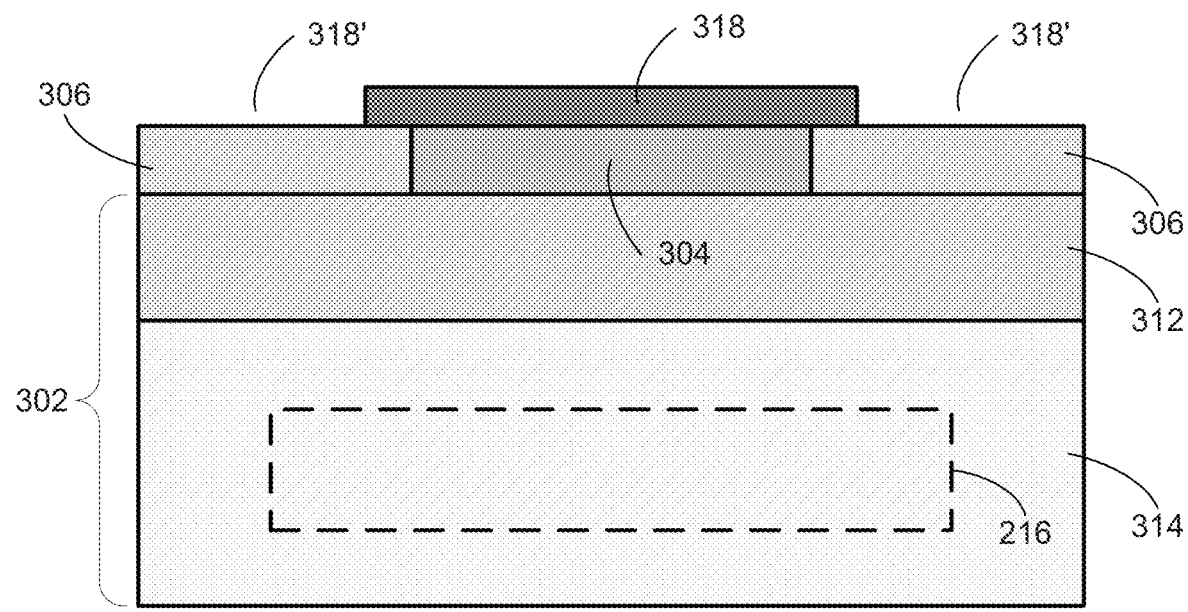

As shown in FIG. 3F, cavities 318' can be formed by removing regions of sacrificial layer 318. In some embodiments, cavities 318' can be formed using a photolithography process where a photoresist layer is applied to the top surface of sacrificial layer 318. Upon exposure to UV light in the desired geometric pattern, regions of the photoresist are dissolved when contacted with a developer solution. An etchant can then be used to selectively etch away the regions of sacrificial layer 318 to form cavities 318'. The regions of sacrificial layer 318 coated with photoresist can be preserved during the etching process, with the photoresist regions being subsequently removed using a liquid resist or plasma stripper.

Figure 3G:
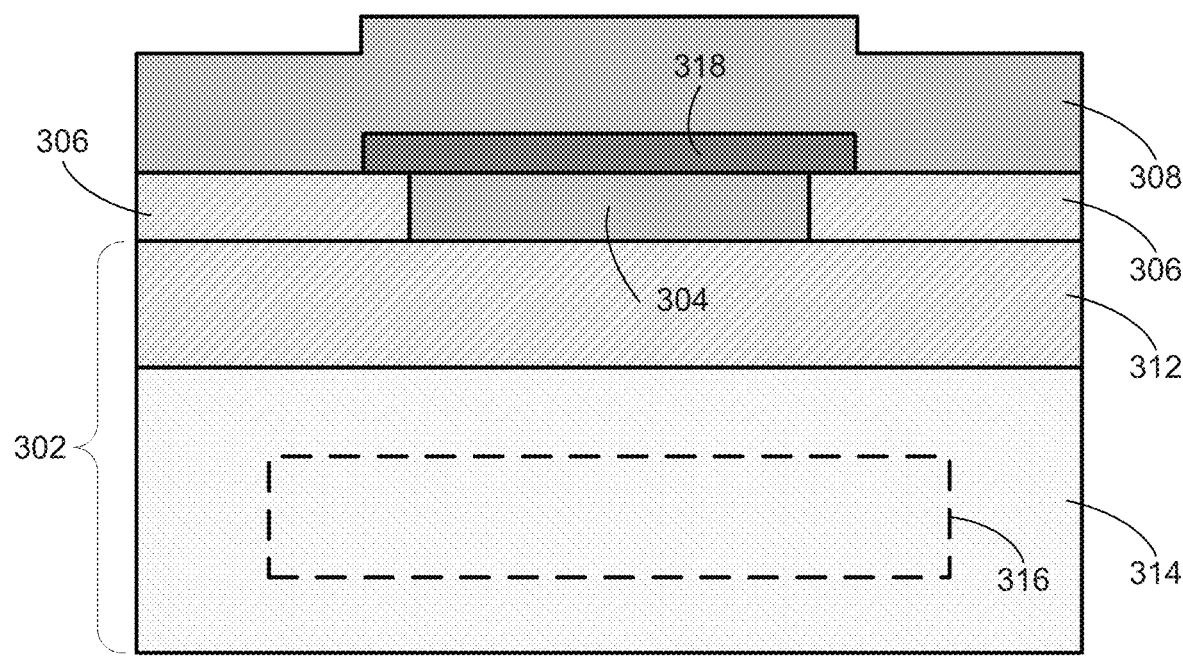

A second electrode 308 can then be deposited onto sacrificial layer 318 and onto a top surface of first dielectric layer 306, as seen in FIG. 3G. Second electrode 308 can be deposited using any suitable deposition technique described herein. As with first electrode 304, second electrode 308 can comprise any suitable electrically conductive material including, but not limited to, metals, semiconductors, carbon, conductive ceramics, and conductive polymers. Exemplary metals can include Cu, W, Ti, Au, Ag, Al, Zn, Ni, Fe, Pt, Ta, and the like. Exemplary semiconductors can include Si, Ge, SiGe, GaAs, InP, and the like. Exemplary carbon allotropes and morphologies can include diamond, graphite, graphene, nanotubes, nanofibers, vapor grown carbon fiber (VGCF), and the like. In some embodiments, carbon-containing compounds can be used as the material for first electrode 204 and second electrode 208. Exemplary conductive ceramics can include TiN, indium tin oxide (ITO), lanthanum-doped strontium titanate (SLT), yttrium-doped strontium titanate (SYT), and the like. Exemplary conductive polymers can include poly(pyrrole)s (PPY), polyanilines (PANI), poly(thiophene)s (PT), poly(3,4-ethylenedioxythiophene) (PEDOT), poly(p-phenyl sulfide) (PPS), poly(acetylene)s (PAC), poly(p-phenylene vinylene) (PPV), and the like.

In some embodiments, first electrode 304 and second electrode 308 can comprise the same electrically conductive material. In other embodiments, first electrode 204 and second electrode 208 can comprise different electrically conductive materials.

First electrode 304 and second electrode 308 can have any suitable orientation with respect to one another. In some embodiments, first electrode 304 and second electrode 308 can be oriented orthogonally to one another. In other embodiments, first electrode 304 and second electrode 308 can be oriented parallel to one another or at any suitable angle between 0 and 180° so long as gap 310 is present between first electrode 304 and second electrode 308.

Figure 3H:
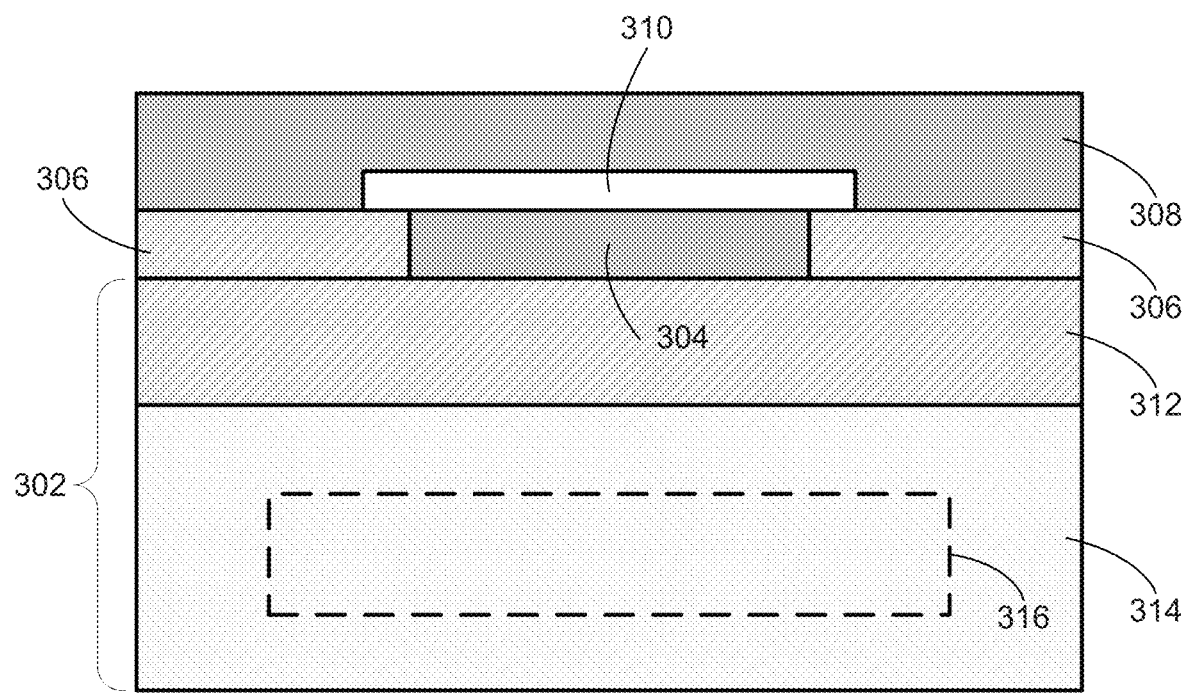

As shown in FIG. 3H, sacrificial layer 318 can be removed to form a gap 310 defined by a top surface of first electrode 304 and a bottom surface of second electrode 308.

In some embodiments, sacrificial layer 318 can be removed by way of an etching process where sacrificial layer is exposed to an etchant. Sacrificial layer 318 can be comprised of any suitable material having a different etch rate than the other materials in the device, such as first electrode 304, second electrode 308, first dielectric layer 306, and substrate 302 (including second dielectric layer 312 and semiconductor substrate 314 in some embodiments). By selecting the appropriate etchant, sacrificial layer 318 can be dissolved with the other materials in the device unaffected by the etchant. Suitable etchants for removing sacrificial layer can include, but are not limited to, hydrofluoric acid, phosphoric acid, hydrochloric acid, nitric acid, sodium hydroxide, SC-1 solution, organic solvents, and $O_2$ plasma.

In FIG. 3G, second electrode 308 has a stepwise structure due to second electrode 308 being a layer of uniform thickness deposited onto both first dielectric layer 306 and sacrificial layer 318 disposed on the top surface of first dielectric layer 306. As seen in FIG. 3H, the stepwise structure can be planarized if desired by way of, for example, a chemical mechanical polishing (CMP) process.

The thickness of sacrificial layer 318, and thus the corresponding width of gap 310, can correspond to a size of a linear biomolecule such that a quantum tunneling current is transmitted between first electrode 304 and second electrode 308 when a voltage is applied across first electrode 304 and second electrode 308 and a part of the linear biomolecule is present in gap 310. In some embodiments, the width of gap 310 can be about 0.8 to 5.0 nm. If the device is to be used to sequence small linear biomolecules such as DNA or RNA, the width of gap 310 can be about 0.8 to 1.2 nm in some embodiments. For larger biomolecules such as polypeptides or proteins, the width of gap 310 can be about 1.2 to 5.0 nm in some embodiments.

In some embodiments, as shown in FIG. 3H, gap 310 can be further defined by a top surface of first dielectric layer 306 and a side surface of second electrode 308. In such embodiments, the top surface of first dielectric layer 306 and the top surface of first electrode 304 can be substantially coplanar. In some other embodiments, first electrode 304 can be recessed such that its top surface is in a plane below that formed by the top surface of first dielectric layer 306. In such embodiments, gap 310 can be further defined by a side surface of first dielectric layer 306, and can be formed as a result of first electrode 304 shown in FIG. 3D being deposited to have a thickness less than the height of cavity 306' shown in FIG. 3C. In this configuration, all or a portion of sacrificial layer 318 shown in FIG. 3E can fill the region of cavity 306' present above first electrode 304.

As described above, if semiconductor substrate 314 is included in substrate 302, semiconductor substrate 314 can include circuitry 316. In some embodiments, circuitry 316 can be electrically coupled to first electrode 304 and second electrode 308. For example, circuitry 316 can be electrically coupled to first electrode 304 using a first via through second dielectric layer 312, and circuitry 316 can be electrically coupled to second electrode 308 using a second via through second dielectric layer 312 and first dielectric layer 306. Circuitry 316 can be configured to apply a voltage across first electrode 304 and second electrode 308, and measure quantum tunneling current transmitted between (or the voltage across) first electrode 304 and second electrode 308.

As described herein, when a part of a linear biomolecule is present in gap 310 and a voltage is applied across first electrode 304 and second electrode 308, a quantum tunneling current can be transmitted between first electrode 304 and second electrode 308. The measured quantum tunneling current (or resulting voltage) can be mapped to the particular part of the biomolecule present in gap 310. Sequencing can be accomplished by repeating the measurements as the biomolecule traverses gap 310. Circuitry 316 can be configured to perform such mapping operations or, alternatively, can transmit current or voltage measurements to an external computing device configured to perform some or all of the mapping operations.

In FIGS. 3A-3H, circuitry 316 is depicted as being contained within semiconductor substrate 314. In other embodiments, all or a portion of circuitry 316 can be present outside substrate 302. For example, one or more transistors, capacitors, resistors, diodes, and/or inductors of circuitry 316 can reside external to substrate 302 or external to the device altogether. In some embodiments, all or a portion of circuitry 316 can be in the form of an external integrated circuit chip or in any other suitable configuration external to the device.

The device formed by the method depicted in FIGS. 3A-3H can be one of many devices on a single integrated circuit chip. For example, the top surface of semiconductor substrate 314 can be large enough to support an array of many devices each including first dielectric layer 306, second dielectric layer 312, first electrode 304, second electrode 308, and gap 310. Accordingly, the methods according to embodiments of the invention can be scaled such that many devices are formed on a single chip simultaneously or sequentially. In some embodiments, each device can be formed to be separated by a dielectric layer to prevent electrodes in adjacent devices from coming into electrical or physical contact with one another. In some embodiments, each device in an array can include its own circuitry (e.g., circuitry 316) for applying voltages and measuring quantum tunneling current or voltage generated within the specific device. In some other embodiments, the circuitry for multiple devices can be integrated such that circuitry 316 applies voltages and measures quantum tunneling currents or voltages when linear biomolecules are present in the gaps of some or all of the devices in the array.

C. Materials Selection

As described above, the precisely dimensioned gap used to sequence linear biomolecules can be formed by depositing a sacrificial layer disposed between two electrodes, and then removing the sacrificial by way of an etching process with the void left behind forming the gap. The materials used for dielectric layers, electrodes, and the sacrificial layer, and a selected etchant, can be chosen such that when the device including the sacrificial layer (e.g., in FIG. 3G) is exposed to the etchant, substantially only the sacrificial layer is dissolved to form the gap with the other materials being preserved. Many different combinations of materials and etchants can be used to achieve the desired gap in accordance with various embodiments of the invention. Some exemplary combinations of materials and etchants are provided below in Table 1.

TABLE 1

| Electrode Material | Dielectric Material | Sacrificial Layer Material | Etchant |
| --- | --- | --- | --- |
| Al (or other metal) | SiO$_2$ | Carbon | O$_2$ plasma |
| TiN | Al$_2$O$_3$ | SiO$_2$ | hydrofluoric acid or other fluorine-containing etchant |

TABLE 1-continued

| Electrode Material | Dielectric Material | Sacrificial Layer Material | Etchant |
| --- | --- | --- | --- |
| TiN | Al$_2$O$_3$ | Si$_3$N$_4$ | hydrofluoric acid or other fluorine-containing etchant |
| Al | SiO$_2$ or Si$_3$N$_4$ | BN | O$_2$ plasma |
| Al | Si$_2$O$_3$ or Si$_3$N$_4$ | TaN | SC1 solution (NH$_4$OH:H$_2$O$_2$:H$_2$O) |
| Ta | SiO$_2$ | Si$_3$N$_4$ | phosphoric acid |

The list of combinations of materials and etchants shown in Table 1 is non-exhaustive and thus not intended to be limiting. Many other possible combinations of materials and etchants having different etch rates can be used according to various embodiments of the invention such that the sacrificial material can be etched away without dissolving the other materials of the device. Etch rates for various materials and etchants can be found in Williams, et al., Etch Rates for Micromachining Processing—Part II, *Journal of Microelectromechanical Systems*, 2003, 12(6), 761-778, which is incorporated by reference herein for all purposes.

III. Method of Using Nanofabricated Device

Embodiments of the invention also provide methods of using a nanofabricated device for sequencing linear biomolecules at the single-molecule level and using quantum tunneling effects. As described above, nanofabricated devices of the present invention can include a gap disposed between two electrodes having small width (e.g., 0.8 to 5.0 nm) and being formed using deposition processes such as ALD. The width of the gap can correspond to the size of a linear biomolecule such as DNA, RNA, a polypeptide, a protein, and the like. When a part of the linear biomolecule (e.g., a nucleobase or amino acid) is present in the gap and a voltage is applied across the electrodes, a change in quantum tunneling current can be measured.

In some embodiments, a baseline quantum tunneling current is present upon applying the voltage such that a measured change in quantum tunneling current can be the difference between the baseline current and the increase (or decrease) in current caused by the part of the linear biomolecule being present in the gap at the time the measurement was taken. In some other embodiments, no quantum tunneling current may be transmitted between the electrodes unless the part of the linear biomolecule is present in the gap. In such embodiments, the change in quantum tunneling current can be the total magnitude of current measured.

Changes in voltage across the electrodes can also be measured to sequence linear biomolecules according to various embodiments of the invention. For example, a current source can be utilized that maintains a constant current across the electrodes. When a part of a linear biomolecule is present in the gap, the impedance of the biomolecule part can cause the voltage across the electrodes to change.

Measured changes in quantum tunneling current or voltage can be mapped to the particular biomolecule part present in the gap at the time the measurement was made. Sequencing can be accomplished by repeating and mapping the measurements as the linear biomolecule traverses the gap. In some embodiments, the measurements can be repeated at time intervals selected based upon the velocity through which the biomolecule traverses the gap.

Figure 4:
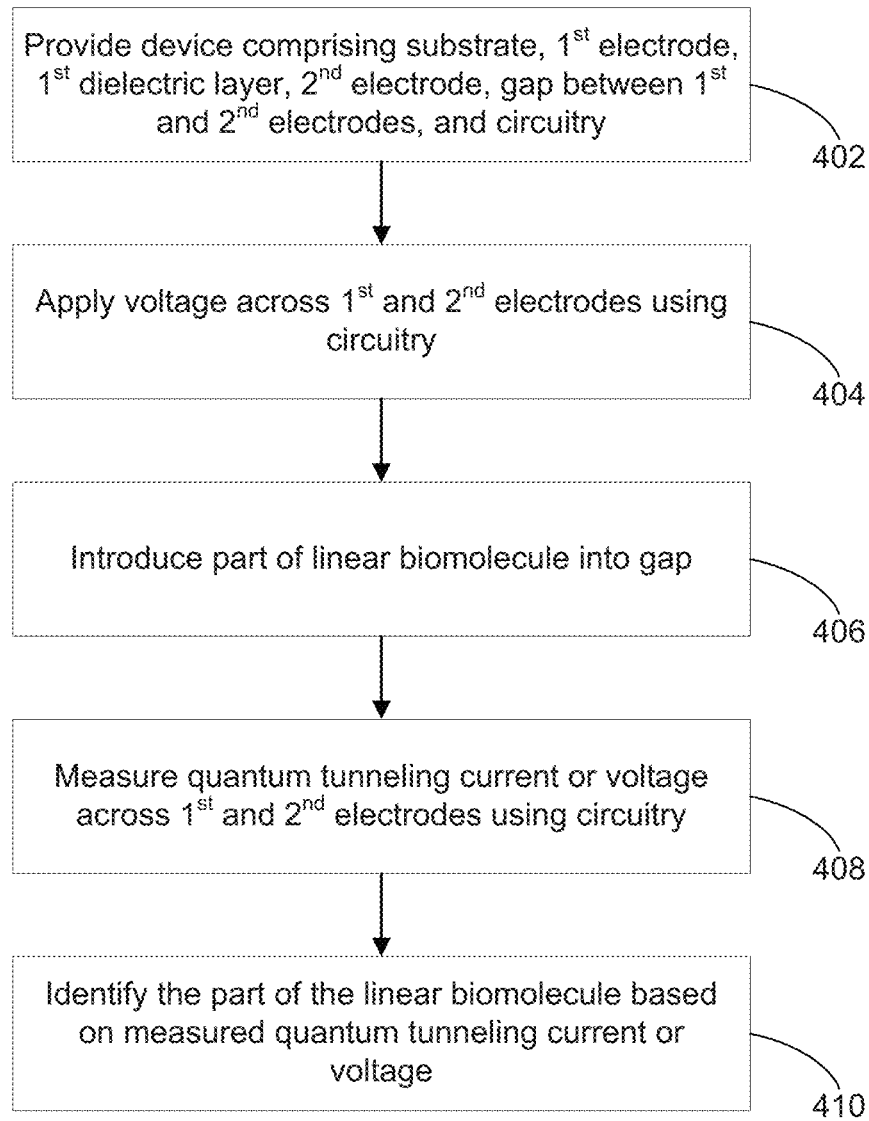
FIG. 4 shows a flowchart illustrating a method of using a device for sequencing a linear biomolecule using quantum tunneling according to embodiments of the present invention.

FIG. 4 shows a flowchart illustrating a method 400 of using a device for sequencing a linear biomolecule using quantum tunneling according to embodiments of the present invention. The device used in method 400 can be device 200 illustrated in FIGS. 2A-2B. Accordingly, all details described above with respect to device 200 can also apply to the device used in method 400.

In step 402, a device can be provided. The device can comprise a substrate having a top surface, a first electrode disposed on a first portion of the top surface of the substrate, a first dielectric layer disposed on a second portion of the top surface of the substrate, and a second electrode disposed on the first dielectric layer and suspended over the first electrode. A gap can be defined by a top surface of the first electrode and a bottom surface of the second electrode.

The provided device can further comprise circuitry electrically coupled to the first electrode and the second electrode. In some embodiments, the substrate of the device can include a second dielectric layer disposed on a semiconductor substrate. In such embodiments, all or part of the circuitry can be included in the semiconductor substrate. For example, the circuitry can be electrically coupled to first electrode using a first via through the second dielectric layer, and the circuitry can be electrically coupled to second electrode using a second via through the second dielectric layer and the first dielectric layer.

In step 404, a voltage can be applied across the first electrode and the second electrode using the circuitry. In some embodiments, the voltage applied can be a constant voltage. In some other embodiments, a varying voltage can be applied by a current source that provides a constant current across the first and second electrodes.

In step 406, a part of a linear biomolecule can be introduced into the gap. In some embodiments, the linear biomolecule can be DNA, RNA, a polypeptide, or a protein. In such embodiments, the part of the linear biomolecule present in the gap can be a nucleobase or a protein.

Many well-known molecular biological protocols, such as protocols for nucleic acid capture, isolating DNA, RNA, or proteins, preparing single-stranded DNA templates, and the like, can be adapted for use in sequencing methods and can be used to prepare the biomolecules for sequencing in accordance with various embodiments of the invention. There are many examples of approaches and commercially available kits for the isolation and creation of single-stranded DNA templates which would be familiar to those skilled in the art, such as the DNA and RNA isolation kits available from Thermo Fisher Scientific, Inc. (Waltham, Mass.). These, however, are only particular examples of many such approaches and are not intended to be limiting.

In some embodiments, the biomolecule can be introduced into the gap by way of one or more channels fabricated either directly on top of the region of the device containing the gap between the electrodes or in a flow cell mounted on the device. The channels can be formed using a large variety of techniques such as machining, molding, pressing, nanofabrication, and the like. The template to be sequenced can be loaded on the device by, for example, placing a droplet of liquid containing the template into a channel Diffusion alone may allow the template to transverse across the electrodes. In some embodiments, since the biomolecules may be charged, they can be directed to flow through the gap by applying an electrical bias down the channel by placing an electrical potential across electrodes located at either end of the channel. The biomolecules can then move electrophoretically down the channel and pass through the gap separating the electrodes. Alternatively, if the biomolecules are large enough, the polarizability of the molecule can be used to move the molecule through the gap using dielectrophoresis as the mechanism. Dielectrophoresis techniques are described in further detail in Ivanov et al., ACS Nano 9 (2015) 3587-3595, which is incorporated by reference herein for all purposes.

In step 408, the circuitry can be used to measure a quantum tunneling current transmitted between the first electrode and the second electrode, the voltage across the first electrode and the second electrode, or an impedance between the first electrode and the second electrode. For example, when the part of the linear biomolecule is present in the gap, its impedance or conductance can cause the current (or voltage) across the first and second electrodes to change. In some embodiments, the change can be relative to a baseline level of current or voltage across the electrodes when no biomolecule is present between them. In other embodiments, the change can be relative to zero current or voltage that reaches a non-zero value only when the linear biomolecule is present.

In step 410, the part of the linear biomolecule introduced into the gap can be identified based on the measured quantum tunneling current, voltage, or impedance. In some embodiments, mapping data including current values, voltage values, and/or impedance values for various linear biomolecule parts can be stored in a data table or other data structure. In some embodiments, the mapping data can be stored within the device. In some other embodiments, the mapping data can be stored in an external computing device that receives the current, voltage, or impedance measurements from the device. In either case, the mapping data can be compared against the current or voltage measurements to determine which linear biomolecule part was present in the gap at the time the measurement was made.

Measurements can be repeated at a time interval based on the velocity at which the linear biomolecule traverses the gap. By mapping the series of measurements to linear biomolecule parts, the biomolecule can thereby be sequenced.

IV. Computer System

One or more of the processes described herein for sequencing linear biomolecules by mapping changes in measured current, voltage, or impedance to specific linear biomolecule parts can be accomplished by a computer system that is incorporated into or external to a nanofabricated device.

Figure 5:
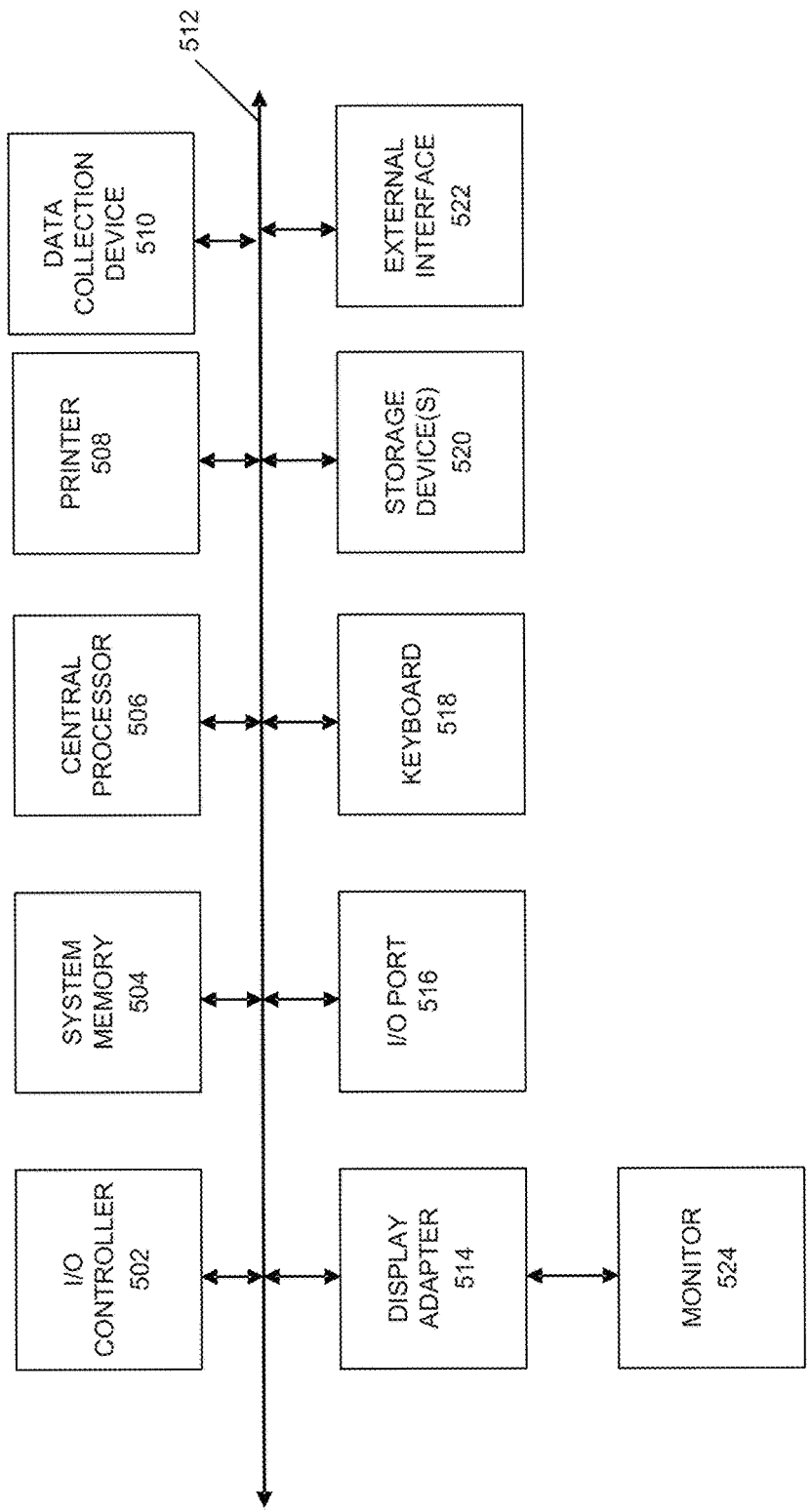
FIG. 5 shows a block diagram of an exemplary computer system usable to sequence linear biomolecules using quantum tunneling according to embodiments of the present invention.

FIG. 5 shows a block diagram of an exemplary computer system 500 usable to sequence linear biomolecules using quantum tunneling according to embodiments of the present invention. As seen in FIG. 5, computer system 500 can utilize a number of subsystems. In some embodiments, computer system 500 can include a single computer apparatus, where the subsystems can be the components of the computer apparatus. In other embodiments, computer system 500 can include multiple computer apparatuses, each being a subsystem, with internal components. Computer system 500 can include one or more desktop computers, laptop computers, tablets, mobile phones, or other types of computing devices.

The subsystems shown in FIG. 5 are interconnected via a system bus 512. Additional subsystems such as a printer 508, keyboard 518, storage device(s) 520, monitor 524, which is coupled to a display adapter 514, and others are shown. Peripherals and input/output (I/O) devices, which couple to I/O controller 502, can be connected to computer system 500 by any number of means known in the art such as input/output (I/O) port 516 (e.g., USB, FireWire®). For example, I/O port 516 or an external interface 522 (e.g. Ethernet, Wi-Fi, etc.) can be used to connect computer system 500 to a wide area network such as the Internet, a mouse input device, or a scanner. The interconnection via system bus 512 allows a central processor 506 to communicate with each subsystem and to control the execution of instructions from system memory 504 or storage device(s) 520 (e.g., a fixed disk, such as a hard drive, or optical disk), as well as the exchange of information between subsystems. System memory 504 and/or storage device(s) 520 may embody a computer readable medium. Another subsystem is a data collection device 510, such as a camera, microphone, accelerometer, or the like. Any of the data mentioned herein can be output from one component to another component and can be output to the user.

Computer system 500 can include a plurality of the same components or subsystems, e.g., connected together by external interface 522 or by an internal interface. In some embodiments, computer systems, subsystems, or apparatuses can communicate over a network. In such instances, one computer can be considered a client and another computer a server, where each can be part of a same computer system. A client and a server can each include multiple systems, subsystems, or components.

The invention claimed is:

1. A device for sequencing a linear biomolecule using quantum tunneling, the device comprising:
   a substrate having a top surface;
   a first electrode disposed on and in contact with a first portion of the top surface of the substrate;
   a first dielectric layer disposed on and in contact with a second portion of the top surface of the substrate, wherein a top surface of the first dielectric layer and a top surface of the first electrode are substantially coplanar;
   a second electrode, wherein:
      a first portion of the second electrode is disposed on and in contact with the top surface of the first dielectric layer, and
      a second portion of the second electrode is suspended over the first electrode, wherein the second portion suspended over the first electrode spans from a first end of the first electrode to an opposite end of the first electrode and is continuous; and
   a gap defined by the top surface of the first electrode, a bottom surface of the second electrode, the top surface of the first dielectric layer, a first side surface of the second electrode, and a second side surface of the second electrode, wherein a width of the gap corresponds to a size of the linear biomolecule such that a quantum tunneling current is transmitted between the first electrode and the second electrode when:
      a voltage is applied across the first electrode and the second electrode; and
      a part of the linear biomolecule is present in the gap;
   wherein:
      the substrate comprises a second dielectric layer in contact with a bottom surface of the first electrode;
      a bottom surface of the first dielectric layer and the bottom surface of the first electrode are substantially coplanar; and
      the second dielectric layer is in contact with the bottom surface of the first dielectric layer.

2. The device of claim 1, wherein the substrate comprises a semiconductor substrate on which the second dielectric layer is disposed.

3. The device of claim 1, wherein the width of the gap is 0.8 to 5.0 nm.

4. The device of claim 1, wherein the first electrode and the second electrode are oriented orthogonally to one another.

5. The device of claim 1, further comprising circuitry electrically coupled to the first electrode and the second electrode, wherein the circuitry is configured to:
   apply the voltage across the first electrode and the second electrode; and
   measure:
      the quantum tunneling current transmitted between the first electrode and the second electrode;
      the voltage across the first electrode and the second electrode; or
      an impedance between the first electrode and the second electrode.

6. The device of claim 1, wherein the first electrode and the second electrode each individually comprises a material selected from a group consisting of metals, semiconductors, carbon, conductive ceramics, and conductive polymers.

7. The device of claim 1, wherein the first dielectric layer comprises a material selected from the group consisting of oxides, dielectric ceramics, polymers, carbonates, glasses, and minerals.

8. The device of claim 1, wherein:
   the bottom surface of the second electrode is between the first side surface of the second electrode and the second side surface of the second electrode,
   a first edge of the bottom surface of the second electrode is a first edge of the first side surface of the second electrode, and
   a second edge of the bottom surface of the second electrode is a first edge of the second side surface of the second electrode.

9. The device of claim 8, wherein the first electrode is disposed within a cavity of the first dielectric layer such that two side surfaces of the first electrode contact the first dielectric layer.

10. The device of claim 9, wherein an edge of the top surface of the first electrode contacts an edge of the top surface of the first dielectric layer.

11. The device of claim 10, wherein a second edge of the first side surface of the second electrode contacts the top surface of the first dielectric layer.

12. The device of claim 11, wherein a second edge of the second side surface of the second electrode contacts the top surface of the first dielectric layer.

13. The device of claim 1, wherein the gap is formed by:
   depositing a sacrificial layer on the top surface of the first electrode,
   depositing the second electrode onto the sacrificial layer and onto the top surface of the first dielectric layer, and
   removing the sacrificial layer.

14. The device of claim 1, wherein the first dielectric layer comprises a piezoelectric element comprising a material that expands in volume in response to an applied electromagnetic field.

15. The device of claim 1, wherein the first dielectric layer and the second dielectric layer comprise different materials.

16. The device of claim 1, wherein the first electrode consists of gold.

17. The device of claim 1, further comprising a via, wherein the via is disposed through the second dielectric layer and is electrically coupled to the first electrode.

18. A sequencing method comprising:
a) providing the device according to claim 1;
b) applying the voltage across the first electrode and the second electrode;
c) introducing the part of the linear biomolecule into the gap;
d) measuring:
   the quantum tunneling current transmitted between the first electrode and the second electrode; and/or
   the voltage across the first electrode and the second electrode; and/or
   an impedance between the first electrode and the second electrode; and
e) identifying, based on the measured quantum tunneling current, the measured voltage, or the measured impedance, the part of the linear biomolecule introduced into the gap.

* * * * *